(12) United States Patent
Lanciault et al.

(10) Patent No.: US 8,262,912 B1
(45) Date of Patent: Sep. 11, 2012

(54) ISOLATED BIOACTIVE COMPOUNDS AND METHOD OF USE

(75) Inventors: David P. Lanciault, Plano, TX (US); Robert N. Ames, Pilot Point, TX (US)

(73) Assignee: Tenfold Technologies, LLC, Pilot Point, TX (US)

( * ) Notice: Subject to any disclaimer, the term of this patent is extended or adjusted under 35 U.S.C. 154(b) by 438 days.

(21) Appl. No.: 12/455,718

(22) Filed: Jun. 5, 2009

(51) Int. Cl.
  *B01D 15/08* (2006.01)
  *A01N 25/00* (2006.01)

(52) U.S. Cl. ............ 210/656; 47/58.1 R; 71/6; 210/774; 210/702; 210/787; 210/804; 210/806; 435/243; 504/116.1; 504/117; 504/118

(58) Field of Classification Search .................. 210/635, 210/656, 702, 737, 770, 774, 787, 804, 806; 71/1, 8–11, 6, 23; 436/161, 177, 178; 435/41, 435/243; 424/115, 123, 124; 47/58.1 R, 47/58.1 C, 58.1 F, 58.1; 504/116.1, 117, 504/118
See application file for complete search history.

(56) References Cited

U.S. PATENT DOCUMENTS

| | | | | |
|---|---|---|---|---|
| 2,556,376 A | * | 6/1951 | Solomons et al. | 424/123 |
| 2,756,134 A | * | 7/1956 | Novak | 71/1 |
| 2,901,864 A | * | 9/1959 | Hiler | 47/58.1 R |
| 4,018,593 A | * | 4/1977 | Muller | 504/117 |
| 4,395,351 A | * | 7/1983 | Camp | 516/9 |
| 5,071,559 A | | 12/1991 | Bleeker | |
| 5,387,271 A | * | 2/1995 | Crawford et al. | 71/9 |
| 6,318,023 B1 | * | 11/2001 | Yamashita | 504/117 |
| 6,336,772 B1 | * | 1/2002 | Yamashita | 405/128.5 |
| 6,521,129 B1 | | 2/2003 | Stamper et al. | |
| 6,761,886 B2 | | 7/2004 | Cheung | |
| 6,828,131 B2 | | 12/2004 | Zhang | |
| 6,927,320 B1 | * | 8/2005 | Benfey et al. | 800/287 |
| 6,979,444 B2 | | 12/2005 | Cheung | |
| 6,994,850 B2 | | 2/2006 | Cheung | |
| 7,014,768 B2 | | 3/2006 | Li et al. | |
| 7,044,994 B2 | | 5/2006 | Porubcan | |
| 7,255,890 B2 | | 8/2007 | Sanz Gutierrez | |
| 8,002,870 B2 | * | 8/2011 | Yamashita | 71/11 |
| 2003/0087454 A1 | * | 5/2003 | Schultz et al. | 436/161 |
| 2004/0154988 A1 | | 8/2004 | Sheets, Sr. | |
| 2006/0027496 A1 | | 2/2006 | Campion et al. | |
| 2006/0130546 A1 | | 6/2006 | Beaton et al. | |
| 2006/0194299 A1 | | 8/2006 | Brinch-Pedersen et al. | |
| 2007/0191228 A1 | * | 8/2007 | Li et al. | 504/117 |
| 2010/0135978 A1 | * | 6/2010 | Svendsen et al. | 424/94.2 |
| 2010/0135987 A1 | * | 6/2010 | Hickman et al. | 424/130.1 |
| 2010/0310548 A1 | * | 12/2010 | Yeh et al. | 424/130.1 |

FOREIGN PATENT DOCUMENTS

| | | |
|---|---|---|
| EP | 287152 | 4/2008 |
| WO | WO9113835 | 9/1991 |
| WO | WO0039052 | 7/2000 |
| WO | WO0044688 | 8/2000 |
| WO | WO02070436 | 9/2002 |

* cited by examiner

*Primary Examiner* — Joseph Drodge
(74) *Attorney, Agent, or Firm* — Schultz & Associates, P.C.

(57) ABSTRACT

Bioactive compounds extracted from a fermentation broth created by a unique microbial community during a fermentation process and fractionated into several fractions based on size. Four of the resulting fractions stimulate growth of plants that are planted in soil to which the fractions have been applied. The fractions can be applied to the soil individually or combined together prior to application. In another embodiment, the unique fractions can be freeze dried or spray dried.

22 Claims, 3 Drawing Sheets

ISOLATED BIOACTIVE COMPOUNDS AND METHOD OF USE

FIELD OF THE INVENTION

The present invention relates to the unique grouping of biological materials containing bioactive compounds and the isolation method thereof from a unique larger microbial community for improving plant growth. Methods of applying the unique grouping of bioactive compounds are also provided.

BACKGROUND OF THE INVENTION

Increasing plant growth and food production is a major concern around the world. As world populations increase, the need for more food production increases as well. However, the available land to produce food is decreasing due to soil degradation, salinity, reduced water quality, increased industrialization, and other land demands.

In addition to decreasing land for agriculture, there is also a demand for the protection of water supplies. Fertilizers and pesticides applied to the soil to increase food production can be washed away and enter surface and groundwater supplies. Nutrient loading of waterways is not healthy for humans or animals, and must be removed before the water is safe to drink or use.

Costs of fertilizers have increased due to energy and transportation costs, thus farm profits are negatively impacted. Farmers must find ways of maximizing the efficiency of fertilizers.

Water quality is decreasing in major agricultural regions of the United States and the world which further impacts the production of agricultural crops.

There are many ways known to increase plant growth, including application of nutrients (fertilizers and plant growth stimulants). The effects of these types of applications, however, are limited by the manner in which the plants and soil absorb and process these nutrients. Further, excess nutrients are usually applied to offset the amount of fertilizers that are leached away by rain and irrigation or that are immobilized or fixed in the soil and thus become unavailable for plant uptake.

It is also known in the industry that certain bacteria and microorganisms assist in plant growth. For example, bacteria are needed to fix atmospheric nitrogen and then convert this nitrogen to a plant-available form. Microorganisms are known to stimulate plant growth through solubilization of phosphorus or mineralization of other nutrients which then become available for plant uptake and growth. For these types of microorganisms to be used in commercial products, they must be maintained in pure, individual culture and mass produced when needed for assembly, possibly with other microorganisms or additives, into a final product. Since microorganisms are living cells, certain storage conditions must be maintained to keep the cells in a viable form.

Also known to science is the fact that interactions of microorganisms with their environment produces bioactive compounds, generally believed to be compounds such as proteins, small peptides, or other types of molecular structures, which can assist the microorganism in improving physical and chemical aspects of the soil, and stimulate plant growth and nutrient uptake in the plant. However, the exact nature and identification of the specific bioactive compounds that create these beneficial effects is still unknown.

Microorganisms and their bioactive compounds when applied to the soil, can stimulate plant root growth thereby increasing nutrient uptake. This improves the utilization of applied fertilizers thus reducing fertilizer loss and environmental impact.

One example of the use of microorganisms is disclosed in U.S. Patent Application No. 2006/0027496 by Campion, et al. In Campion, a lagoon system is described with anaerobic, facultative, and aerobic stratum whereby the aerobic stratum may be artificially induced by aeration, and additional aerobic bacteria may be artificially added. The system is designed to treat a manure slurry, and the liquid thereof, extracted from the aerobic stratum, may be applied to land as a fertilizer without further processing. Campion mentions the presence of "byproducts" and "growth stimulators" in the lagoon system design, but only in the context that these compounds provide nutrients or otherwise support bacterial fermentation and methanogenesis. Thus the bioactive compounds described by Campion function internally within the lagoon system to process a raw manure slurry. The biological content of the lagoon liquid is not disclosed.

An example of the use of a microbial community to produce a material to stimulate plant growth are products sold by Advanced Microbial Solutions, LLC (AMS) of Pilot Point, Tex. under the trade names SuperBio® SoilBuilder™, SuperBio® AgBlend™, SuperBio® SoilLife™, and NutriLife. These products are sold by AMS and its licensees across the United States and overseas. These products are created from a unique community of microbes and biological material after a fermentation process. The AMS fermentation system results in the production of a fermentation extract solution containing live microorganisms and bioactive compounds. The base fermentation extract solution is sold as SuperBio® SoilBuilder™, and serves as the primary ingredient for additional commercial products identified above. The fermentation extract solution contains many different species of microorganisms and many different bioactive compounds. However, it is unknown which specific types of bioactive compounds or the interaction between them produce the beneficial effects shown by the use of the fermentation extract solution of the prior art.

SUMMARY OF THE INVENTION

The solution disclosed by Applicant begins as a liquid fermentation extract solution containing both microorganisms and bioactive compounds. The fermentation extract solution is the liquid sold as SuperBio® Soilbuilder™. The invention is the use of a known protein extraction method which leads to the concentration of bioactive compounds which are not identified as proteins with standard protein identification techniques.

The original fermentation extract solution is clarified by centrifugation or filtration to remove suspended materials and microorganisms and to separate the microorganisms from the bioactive compounds. For the purposes of this patent application, bioactive compounds are defined as those biochemical compounds of microbial origin which consist of many different types of molecular structures.

In one embodiment, the clarified liquid containing the bioactive compounds is mixed with a saturated solution of ammonium sulfate to precipitate out proteins and other bioactive compounds. The precipitate is concentrated by centrifugation and separated from the remaining solution, redissolved in sterile phosphate buffer, and treated by dialysis to remove ammonium sulfate. The precipitate is then fractionated by size exclusion chromatography to obtain seven fractions.

Fractions 1, 2, 4 and 6 are separated from the remaining three fractions. Each of these fractions, when applied to the soil, either individually or in combinations thereof, generates a growth response in the plants that are planted in the treated soil. The materials in the fractions stimulate plant growth, including but not limited to root growth, shoot growth, number of blooms per plant, number of fruit from each plant, and overall size.

In one embodiment of the invention, fractions 1, 2, 4 and 6 are individually diluted with water prior to application to soil. In another embodiment of the invention, fractions 1, 2, 4 and 6 are combined together in different combinations prior to dilution.

The diluted fraction or fractions are applied to the soil by hand, by sprayers or by plane.

In another embodiment the diluted fractions are mixed with other nutrients, fertilizers, or compounds that promote plant growth or improve the quality of the soil, prior to dilution or application.

In another embodiment, the fractions are freeze dried and subsequently re-dissolved in an aqueous solution prior to application to the soil.

In another embodiment, the fractions are spray dried and subsequently re-dissolved in an aqueous solution prior to application to the soil.

DETAILED DESCRIPTION OF THE PREFERRED EMBODIMENT

SuperBio® SoilBuilder™ is a commercially available product to be applied to the soil to promote plant growth and improve the quality of the soil and is sold to the general public through AMS and its licensees in both the United States and around the world. SuperBio® SoilBuilder™ is the starting point for the present invention. Anyone desiring a sample of SuperBio® SoilBuilder™ can contact AMS or its licensees to purchase such sample.

In one embodiment of the invention, microorganisms are separated from SuperBio® Soilbuilder™ by filtration using sterile 0.45 and 0.022 μm membrane filters or by centrifugation at sufficient rpm to form a pellet and clarify the solution. Filtration and centrifugation removes suspended materials and microorganisms, including bacteria, and results in a clarified liquid which contains only bioactive compounds.

The clarified liquid is mixed with a saturated solution of ammonium sulfate, allowing bioactive compounds to precipitate out of the clarified liquid. The precipitate of bioactive compounds is recovered by use of centrifugation. The precipitate will result in a pellet. The use of saturated solution of ammonium sulfate is known in the art to precipitate and separate out proteins from other compounds.

The pellet or subsequently derived powder of the precipitate is re-dissolved in sterile phosphate buffer and treated by dialysis to remove the ammonium sulfate and equilibrate in phosphate buffered saline (PBS). The resulting solution is then fractionated by size exclusion chromatography. One such method of chromatography which can perform the size exclusion separations is the Superdex 200 column (MWC=200 kDa). The column eluate extracts are obtained over time and combined into seven fractions from the ninety (90) originally obtained.

Figure 1:
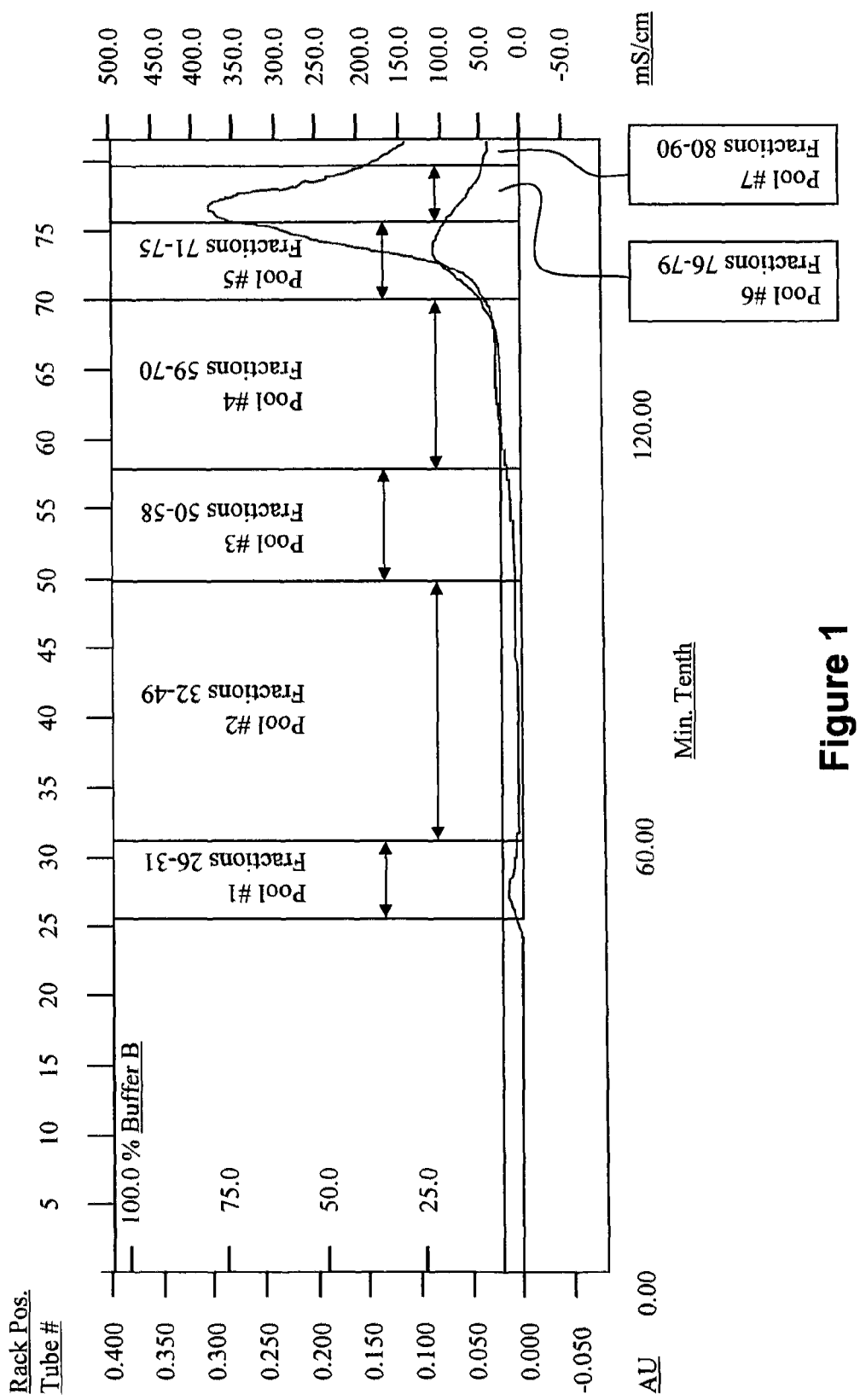
FIG. 1 is the graph chromatography results for the seven sample fractions.

FIG. 1 illustrates the seven fractions resulting from the size exclusion chromatography. Fraction 1 encompasses the materials collected in tubes 26 through 31 and contains the largest compounds. Fraction 2 encompasses the materials collected in tubes 32 through 49 and contains the next smallest compounds. Fraction 3 encompasses the materials collected in tubes 50 through 58 and contains the next smallest compounds. Fraction 4 encompasses the materials collected in tubes 59 through 70 and contains the next smallest compounds. Fraction 5 encompasses the materials collected in tubes 71 through 75 and contains the next smallest compounds. Fraction 6 encompasses the materials collected in tubes 76 through 79 and contains the next smallest compounds. Fraction 7 encompasses the materials collected in tubes 80 through 90 and contains the smallest compounds.

Fractions 1, 2, 4 and 6 are separated from the remaining three fractions. Each of these fractions, when applied to the soil, either individually or in combinations thereof, generates a plant growth response in the plants that are in the treated soil. The materials in the fractions stimulate plant growth, including but not limited to root growth, shoot growth, number of blooms per plant, number of fruit from each plant, and overall size.

The seven fractions were analyzed by SDS-PAGE (sodium dodecyl sulfate polyacrylamide gel electrophoresis) and treated with a coomassie stain to confirm size fractionation and the presence of proteins. Even though the separation method used is intended to precipitate out proteins and it was anticipated that proteins would be found, proteins were not identified or observed in the fractions. This result was confirmed by the use of UV scans and mass spectrometry and no proteins were identified in fractions 1, 2, 4 and 6. This was a surprising result.

In one embodiment of the invention, fractions 1, 2, 4 and 6 are individually diluted with water prior to application to soil. Fraction 1 is diluted in the range of about 1:300 to 1:400 by volume. Fraction 2 is diluted in the range of about 1:100 to 1:200 by volume. Fraction 4 is diluted in the range of about 1:100 to 1:200 by volume. Fraction 6 is diluted in the range of about 1:500 to 1:600 by volume.

In another embodiment of the invention, fractions 1, 2, 4 and 6 are combined together prior to dilution. When fractions 1 and 2 are combined, they are diluted in the range of about 1:50 to 1:150 by volume. When fractions 1 and 4 are combined, they are diluted in the range of about 1:100 to 1:200 by volume. When fractions 1 and 6 are combined, they are diluted in the range of about 1:200 to 1:300 by volume. When fractions 2 and 4 are combined, they are diluted in the range of about 1:50 to 1:150 by volume. When fractions 2 and 6 are combined, they are diluted in the range of about 1:50 to 1:150 by volume. When fractions 4 and 6 are combined, they are diluted in the range of about 1:100 to 1:200 by volume. When fractions 1, 2, and 4 combined, they are diluted in the range of about 1:25 to 1:125 by volume. When fractions 1, 2, and 6 are combined, they are diluted in the range of about 1:50 to 1:150 by volume. When fractions 1, 4, and 6 are combined, they are diluted in the range of about 1:50 to 1:150 by volume. When fractions 2, 4, and 6 are combined, they are diluted in the range of about 1:50 to 1:150 by volume. When fractions 1, 2, 4, and 6 are combined, they are diluted in the range of about 1:15 to 1:115 by volume.

The diluted fraction or fractions are then applied to the soil. The diluted fractions or fractions can be applied by hand, by sprayer located on the ground or by plane or overhead sprayers.

The fractions can be mixed with other nutrients, fertilizers, or compounds that promote plant growth or improve the quality of the soil, prior to dilution or application.

The application rate per acre of the fraction after dilution is about 1 to 2 gallons per acre.

Fractions 1, 2, 4, and 6 can also be freeze dried or spray dried by techniques known in the art. This is possible since fractions 1, 2, 4, and 6 do not contain any microorganisms that would be killed during the freeze drying or spray drying processes.

Further, since fractions 1, 2, 4, and 6 do not contain microorganisms, the products have a longer shelf life and do not require storage conditions necessary to keep microorganisms alive.

Freeze drying and spray drying allows for easier transportation and storage. The fractions which have been freeze dried or spray dried will be re-hydrated during the dilution process.

The growth response is not limited to a single type of plant or specific genus of plants.

Example One

One example of effectiveness of fractions on pepper plants to stimulate plant growth is documented below. Pepper plants were chosen since they are representative of important agricultural crops. The growth response documented with pepper plants would be representative of other plant species.

Pepper plants were grown from seeds and selected for uniformity of transplant size. Five plants were used for each of the four fractions, the original SuperBio® SoilBuilder™, and a control. The pepper plants were transplanted into six-inch pots with 1800 cm$^3$ of potting soil.

Each fraction was individually diluted to create 500 mL of solution. The amount of fraction 1 diluted was 1.3 mL. The amount of fraction 2 diluted was 4.2 mL. The amount of fraction 4 diluted was 2.9 mL. The amount of fraction 6 diluted was 0.9 mL. The amount of SoilBuilder™ diluted was 15.0 mL. The control was 500 mL of water. After each plant was transplanted, 100 mL of the respective solution was applied evenly around the base of the respective plant. Water and the same fertilizer were applied to all the pepper plants in the same quantity on a weekly basis. The fertilizer used was Scotts, Peters Professional Pete-Lite Special water soluble fertilizer (20-10-20) with trace nutrients and was dissolved in water at 1 pound/100 gallons (454 g/378.5 L).

Plants were harvested approximately 35 days after transplanting. Fresh roots and shoots, dry roots and shoots, number of blooms, and number of fruit were measured. The resulting means from the measurements of the five plants per treatment are as follows in Table 1 below.

These results show that the individualized fractions perform better once isolated that in the original SuperBio® SoilBuilder™ product, which included the three remaining fractions and the suspended materials and microorganisms. It is further evidenced that fractions 1 and 6 are most stimulatory for root growth and fractions 1 and 4 were most stimulatory for shoot growth.

The effects of the materials in fractions 1, 2, 4, and 6 are sustained. These fractions were tested again six months after fractionization. The fractions were kept refrigerated at 4° C. since fractionization. This additional example documents the long-term effects of bioactive compounds in these fractions.

Example 2

Pepper plants were grown from seeds and thirty plants were selected based on uniformity of transplant size. Five plants were used for each of fractions 1, 2, 4, and 6, the SuperBio® SoilBuilder™, and a control. The pepper plants were transplanted into six-inch pots with 1800 cm$^3$ of potting soil.

Each of the fractions and the SuperBio® SoilBuilder™ were individually diluted to create 500 mL of solution for application to the pepper plants. The amount of fraction 1 diluted was 1.3 mL. The amount of fraction 2 diluted was 4.2 mL. The amount of fraction 4 diluted was 2.9 mL. The amount of fraction 6 diluted was 0.9 mL. The amount of SoilBuilder™ diluted was 15.0 mL. The control was 500 mL of water.

After the first group of five pepper plants was transplanted, 100 mL of the fraction 1 diluted solution was applied evenly around the base of each of the five plants. After the second group of five pepper plants was transplanted, 100 mL of fraction 2 diluted solution was applied evenly around the base of each of the five plants. After the third group of five pepper plants was transplanted, 100 mL of fraction 4 diluted solution was applied evenly around the base of each of the five plants. After the fourth group of five pepper plants was transplanted, 100 mL of the fraction 6 diluted solution was applied evenly around the base of each of the five plants. After the fifth group of five pepper plants was transplanted, 100 mL of the diluted SuperBio® SoilBuilder™ solution was applied evenly around the base of each of the five plants. After the sixth group of five pepper plants was transplanted, 100 mL of the control water was applied evenly around the base of each of the five plants. Water and the same fertilizer were applied to all the pepper plants in the same quantity on a weekly basis. As with example 1, the fertilizer used was Scotts, Peters Professional Pete-Lite Special water soluble fertilizer (20-10-20) with trace nutrients and was dissolved in water at 1 pound/100 gallons (454 g/378.5 L).

TABLE 1

| Treatment | Root Fresh Wt. (g) | Shoot Fresh Wt. (g) | Total Fresh Wt. (g) | Dry Root Wt. (g) | Dry Shoot Wt. (g) | Total Dry Wt. (g) | Number of Blooms | Number of Fruit |
|---|---|---|---|---|---|---|---|---|
| Fraction 1 | 20.70a | 35.30ab | 55.99ab | 1.65a | 4.00ab | 5.65ab | 3.00abc | 2.00ab |
| Fraction 2 | 19.42abc | 34.18bc | 53.60abc | 1.50abc | 3.73bc | 5.23bcd | 2.60bc | 1.00b |
| Fraction 4 | 19.18abc | 38.24a | 57.42a | 1.58abc | 4.28a | 5.86a | 4.40a | 3.00a |
| Fraction 6 | 19.49ab | 31.50cd | 50.99bcd | 1.65a | 3.89abc | 5.54abc | 2.80abc | 1.40b |
| SoilBuilder ™ | 18.48abc | 32.82bcd | 51.30bcd | 1.44abc | 3.76bc | 5.20bcd | 2.20c | 1.2b |
| Control | 16.9bc | 30.49d | 47.40d | 1.41bc | 3.67bc | 5.08bcd | 4.0ab | 1.6ab |
| LSD$_{0.05}$ | 2.88 | 3.34 | 5.33 | 0.238 | 0.40 | .058 | 1.65 | 1.42 |

Results followed by the same letter within a column are not significantly different at P = 0.05.

Twenty-nine days after transplanting and application of solutions, the number of first blooms was counted. The average of first blooms per plant per treatment are given in Table 2 below.

TABLE 2

| Treatment | Average number of blooms per treatment |
|---|---|
| Fraction 1 | 2.8** |
| Fraction 2 | 2.6** |
| Fraction 4 | 2.4** |
| Fraction 6 | 2.8** |
| SoilBuilder ™ | 2.6** |
| Control | 0.4 |
| $LSD_{0.01}$ | 1.3 |

**Indicates a significantly higher measurement compared to control at P = 0.01

Plants were harvested approximately 43 days after transplanting. Average number of blooms, average number of fruit, average weight of fruit, height, weight of fresh shoots, and weight of fresh roots was determined. The resulting average measures for the fresh roots and shoots, dry roots and shoots, number of blooms, and number of fruit were measured are given in Table 3 below.

TABLE 3

| Treatment | Root Fresh Wt. (g) | Shoot Fresh Wt. (g) | Height (cm) | Average number of blooms | Average number of fruit | Average fruit weight (g) |
|---|---|---|---|---|---|---|
| Fraction 1 | 28.6 | 70.74 | 41.4 | 7.8* | 3.6* | 36.3* |
| Fraction 2 | 34.3* | 90.10* | 47.2* | 9.2* | 3.6* | 33.1* |
| Fraction 4 | 36.4* | 89.42* | 45.0 | 7.0 | 3.8* | 35.5* |
| Fraction 6 | 31.2 | 74.34 | 45.6 | 6.2 | 2.8 | 42.3* |
| Soil-Builder ™ | 34.5* | 71.94 | 42.8 | 6.8 | 4.2* | 48.7* |
| Control | 25.7 | 67.62 | 43.4 | 4.8 | 1.8 | 10.6 |
| $LSD_{0.05}$ | 5.7 | 13.40 | 3.7 | 2.6 | 1.1 | 9.2 |

*Indicates a significantly higher measurement compared to control at P = 0.05

Figure 2:
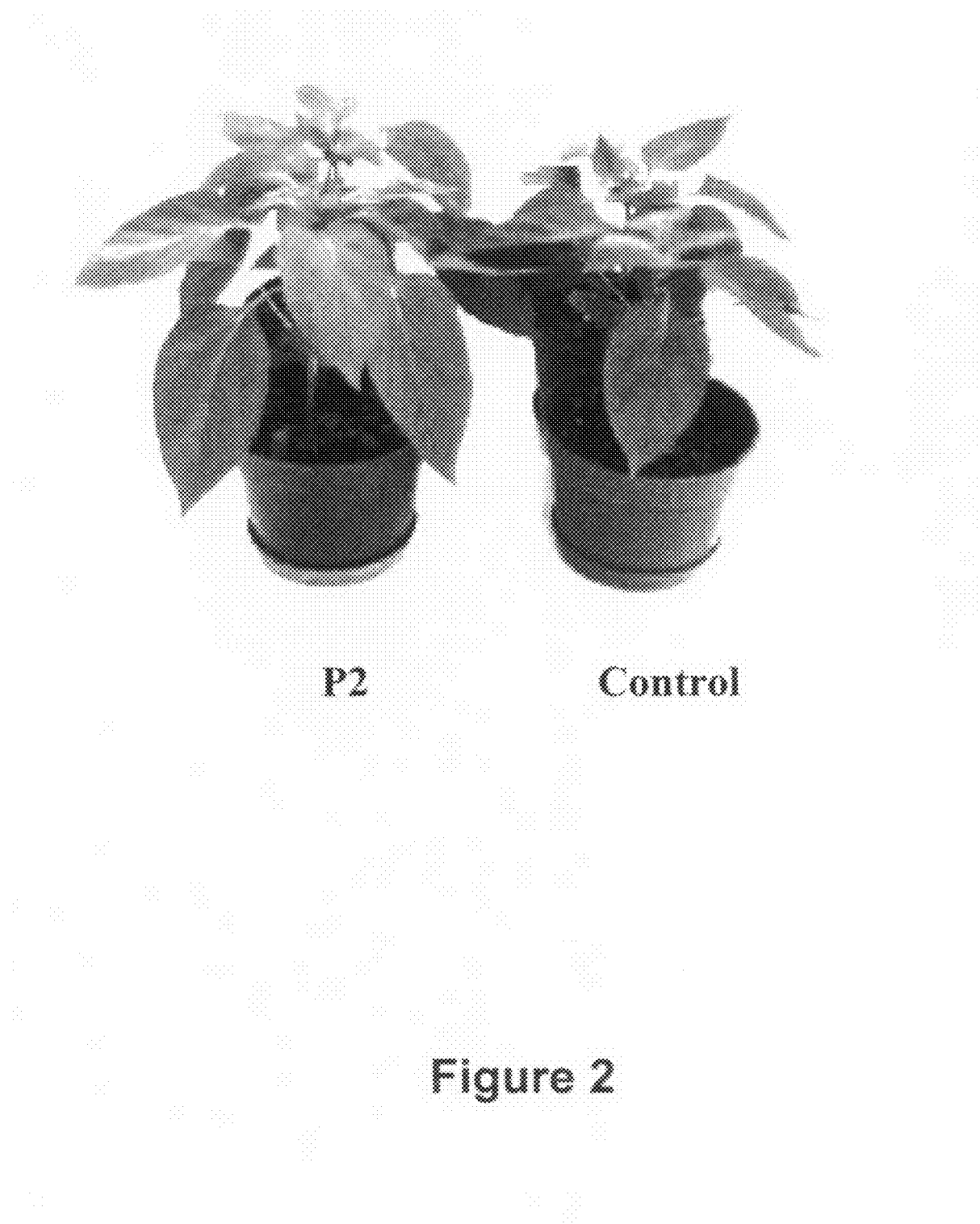
FIG. 2 is photograph of results caused by use of invention.

Pictures of a representative pepper plant to which fraction 2 diluted solution was applied and a pepper plant to which the control solution was applied is shown in FIG. 2.

Figure 3:
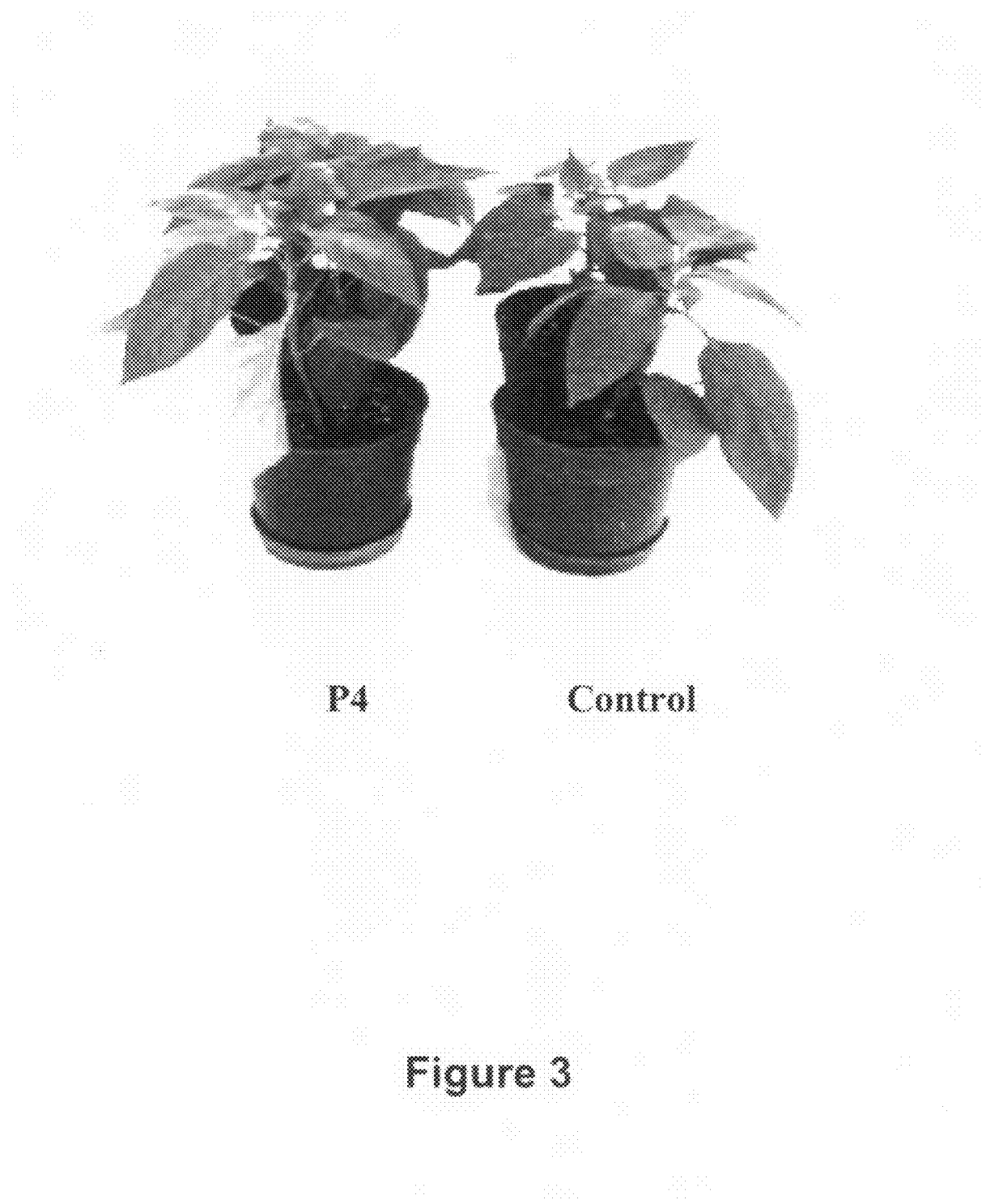
FIG. 3 is photograph of results caused by use of invention.

Pictures of a representative pepper plant to which fraction 4 dilution solution was applied and a pepper plant to which the control solution was applied is shown in FIG. 3.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method of isolating bioactive compounds comprising:
apportioning an amount of a fermentation extract solution;
removing biological matter resulting in a clarified liquid;
mixing the clarified liquid with ammonium sulfate solution resulting in a precipitate;
isolating the precipitate by centrifugation;
redissolving the precipitate in a phosphate buffer;
fractionizing the redissolved precipitate into seven fractions, each fraction sequentially decreasing in compound size;
removing a set of one or more chosen fractions of the seven fractions and,
applying the set of one or more chosen fractions to a portion of soil media adjacent a plant,
wherein a plurality of the seven fractions are capable of stimulating plant growth in a plant that is in the treated soil.

2. The method of isolating bioactive compounds of claim 1 wherein the step of fractionizing comprises fractionizing the precipitate with size exclusion chromatography, wherein the molecular weight cut-off is about 200 kDa; and
wherein the step of removing a set of one or more chosen fractions further comprises removing a fraction having an elution time window of about 52 to about 62 minute tenths.

3. The method of isolating bioactive compounds of claim 1 wherein the step of fractionizing comprising fractionizing the precipitate with size exclusion chromatography, where the molecular weight cut-off is about 200 kDa; and
wherein the step of removing a set of one or more chosen fractions further comprises removing a fraction having an elution time window of about 62 to about 98 minute tenths.

4. The method of isolating bioactive compounds of claim 1 wherein the step of fractionizing comprises fractionizing the precipitate with size exclusion chromatography, where the molecular weight cut-off is about 200 kDa; and
wherein the step of removing a set of one or more chosen fractions further comprises removing a fraction having an elution time window of about 118 to about 140 minute tenths.

5. The method of isolating bioactive compounds of claim 1 wherein the step of fractionizing includes comprises fractionizing the precipitate with size exclusion chromatography, where the molecular weight cut-off is about 200 kDa; and
wherein the step of removing a set of one or more chosen fractions further comprises removing a fraction having an elution time window of about 152 to about 158 minute tenths.

6. The method of isolating bioactive compounds of claim 1 wherein the step of fractionizing includes comprises fractionizing the precipitate with size exclusion chromatography, where the molecular weight cut-off is about 200 kDa; and
wherein the step of removing a set of one or more chosen fractions further comprises removing a primary fraction having an elution time window of about 52 to about 62 minute tenths and a secondary fraction having an elution time window of about 62 to about 98 minute tenths.

7. The method of isolating bioactive compounds of claim 1 wherein the step of fractionizing includes comprises fractionizing the precipitate with size exclusion chromatography, where the molecular weight cut-off is about 200 kDa; and
wherein the step of removing a set of one or more chosen fractions further comprises removing a primary fraction having an elution time window of about 52 to about 62 and a secondary fraction having an elution time window of about 118 to about 140 minute tenths.

8. The method of isolating bioactive compounds of claim 1 wherein the step of fractionizing includes comprises fractionizing the precipitate with size exclusion chromatography, where the molecular weight cut-off is about 200 kDa; and
wherein the step of removing a set of one or more chosen fractions further comprises removing a primary fraction having an elution time window of about 52 to about 62 and a secondary fraction having an elution time window of about 152 to about 158 minute tenths.

9. The method of isolating bioactive compounds of claim 1 wherein the step of fractionizing includes comprises fractionizing the precipitate with size exclusion chromatography, where the molecular weight cut-off is about 200 kDa; and wherein the step of removing a set of one or more chosen fractions further comprises removing a primary fraction having an elution time window of about 62 to about 98 and a secondary fraction having an elution time window of about 118 to about 140 minute tenths.

10. The method of isolating bioactive compounds of claim 1 wherein the step of fractionizing includes the further step of comprises fractionizing the precipitate with size exclusion chromatography, where the molecular weight cut-off is about 200 kDa; and wherein the step of removing a set of one or more chosen fractions further comprises removing a primary fraction having an elution time window of about 62 to about 98 and a secondary fraction having an elution time window of about 152 to about 158 minute tenths.

11. The method of isolating bioactive compounds of claim 1 wherein the step of fractionizing includes comprises fractionizing the precipitate with size exclusion chromatography, where the molecular weight cut-off is about 200 kDa; and wherein the step of removing a set of one or more chosen fractions further comprises removing a primary fraction having an elution time window of about 118 to about 140 and a secondary fraction having an elution time window of about 152 to about 158 minute tenths.

12. The method of isolating bioactive compounds of claim 1 wherein the step of fractionizing includes the further step of comprises fractionizing the precipitate with size exclusion chromatography, where the molecular weight cut-off is about 200 kDa; and wherein the step of removing a set of one or more chosen fractions further comprises removing a primary fraction having an elution time window of about 52 to about 62 minute tenths, a secondary fraction having an elution time window of about 62 to about 98 minute tenths and a tertiary fraction having an elution time window of about 118 to about 140 minute tenths.

13. The method of isolating bioactive compounds of claim 1 wherein the step of fractionizing includes comprises fractionizing the precipitate with size exclusion chromatography, where the molecular weight cut-off is about 200 kDa; and wherein the step of removing a set of one or more chosen fractions further comprises removing a primary fraction having an elution time window of about 52 to about 62 minute tenths, a secondary fraction having an elution time window of 62 to about 98 minute tenths, and a tertiary fraction having an elution time window of about 152 to about 158 minute tenths.

14. The method of isolating bioactive compounds of claim 1 wherein the step of fractionizing includes comprises fractionizing the precipitate with size exclusion chromatography, where the molecular weight cut-off is about 200 kDa; and wherein the step of removing a set of one or more chosen fractions further comprises removing a primary fraction having an elution time window of about 62 to about 98 minute tenths, a secondary fraction having an elution time window of about 118 to about 140 minute tenths, and a tertiary fraction having an elution time window of about 152 to about 158 minute tenths.

15. The method of isolating bioactive compounds of claim 1 wherein the step of fractionizing includes comprises fractionizing the precipitate with size exclusion chromatography, where the molecular weight cut-off is about 200 kDa; and where the step of removing a set of one or more chosen fractions further comprises removing a primary fraction having an elution time window of about 52 to about 62 minute tenths, a secondary fraction having an elution time window of about 62 to about 98 minute tenths, and a tertiary fraction having an elution time window of about 152 to about 158 minute tenths.

16. The method of isolating bioactive compounds of claim 1 further comprising the step of freeze drying the set of one or more chosen fractions.

17. The method of isolating bioactive compounds of claim 1 further comprising the step of spray drying the set of one or more chosen fractions.

18. The method of isolating bioactive compounds of claim 1 further comprising removing the biological matter by filtration.

19. The method of isolating bioactive compounds of claim 1 further comprising removing the biological matter by centrifugation.

20. The method of isolating bioactive compounds of claim 1 further comprising the step of removing the ammonium sulfate from the precipitate by dialysis.

21. The method of isolating bioactive compounds of claim 1 comprising an initial step of obtaining the fermentation extract solution from a commercial product selected from the group consisting of the group of SuperBio® SoilBuilder™ solution, SuperBio® AgBlend™ solution, SuperBio® SoilLife™ solution, and NutriLife solution.

22. The method of isolating bioactive compounds of claim 1 wherein the step of fractionizing the precipitate includes the steps of fractionizing the precipitate by size exclusion chromatography where the molecular weight cut-off is about 200 kDa; and fractionizing the precipitate into:
a first fraction having an elution time window of about 52 to about 62 minute tenths;
a second fraction having an elution time window of about 62 to about 98 minute tenths;
a third fraction having an elution time window of about 98 to about 118 minute tenths;
a fourth fraction having an elution time window of about 118 to about 140 minute tenths;
a fifth fraction having an elution time window of about 140 to about 152 minute tenths;
a sixth fraction having an elution time window of about 152 to about 158 minute tenths;
and a seventh fraction having an elution time window of about 158 to about 168 minute tenths.

* * * * *